(12) United States Patent
Lerg et al.

(10) Patent No.: US 6,706,673 B2
(45) Date of Patent: *Mar. 16, 2004

(54) COSMETIC AND DERMATOLOGICAL DETERSIVE PREPARATIONS CONTAINING ACRYLATE COPOLYMERS, ALKYL GLUCOSIDES AND ALCOHOLS

(75) Inventors: Heike Lerg, Hamburg (DE); Robert Schmucker, Hamburg (DE)

(73) Assignee: Beiersdorf AG, Hamburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/053,342

(22) Filed: Apr. 1, 1998

(65) Prior Publication Data

US 2002/0004467 A1 Jan. 10, 2002

(30) Foreign Application Priority Data

Apr. 8, 1997 (DE) .......................... 197 14 424

(51) Int. Cl.$^7$ .............................. C11D 1/66; C11D 3/37
(52) U.S. Cl. ...................... 510/119; 510/130; 510/470; 510/476
(58) Field of Search .................. 510/158, 159, 510/403, 404, 434, 470, 476, 119, 130

(56) References Cited

U.S. PATENT DOCUMENTS

| 4,678,595 A | | 7/1987 | Malik et al. | |
| 5,145,665 A | * | 9/1992 | Klueppel et al. | 424/50 |
| 5,240,633 A | * | 8/1993 | Ahmed et al. | 252/99 |

(List continued on next page.)

FOREIGN PATENT DOCUMENTS

| DE | 43 06 899 A1 | 9/1994 |
| DE | 43 27 700 A1 | 2/1995 |
| EP | 0 194 097 A1 | 9/1986 |
| EP | 0 384 983 A2 | 9/1990 |
| EP | 0 422 862 A2 | 4/1991 |
| EP | 0 603 078 A1 | 6/1994 |
| EP | 0 678 294 A2 | 10/1995 |
| FR | 2 731 616 A1 | 9/1996 |
| WO | WO 96/02225 | 2/1996 |
| WO | WO 98/47474 | 10/1998 |

OTHER PUBLICATIONS

Derwent Abstract of FR2731616A.
XP 002121408 Abstract of Chemical Abstracts, vol. 117, No. 18, Nov. 2, 1992.

(List continued on next page.)

Primary Examiner—John Hardee
(74) Attorney, Agent, or Firm—Norris McLaughlin & Marcus

(57) ABSTRACT

Cosmetic and dermatological detersive preparations comprising:
(a) an effective amount of one or more surface-active substances selected from the group consisting of alkyl glucosides, which have the structural formula

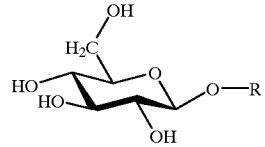

where R is a branched or unbranched alkyl radical having from 1 to 24 carbon atoms,
(b) an effective amount of one or more gel-forming acrylate-alkyl acrylate copolymers and
(c) branched and/or unbranched aliphatic alcohols having 2–6 carbon atoms and one or more OH functions.

11 Claims, 1 Drawing Sheet

U.S. PATENT DOCUMENTS

| | | | | |
|---|---|---|---|---|
| 5,409,640 A | * | 4/1995 | Giret et al. | 252/546 |
| 5,464,874 A | * | 11/1995 | Balzer | 514/777 |
| 5,582,816 A | * | 12/1996 | Mandanas et al. | 424/49 |
| 5,610,125 A | * | 3/1997 | Zimmerman | 510/123 |
| 5,610,212 A | * | 3/1997 | Tanaka et al. | 524/156 |
| 5,629,366 A | * | 5/1997 | Rogiers et al. | 524/56 |
| 5,631,003 A | * | 5/1997 | Mueller et al. | 424/70.31 |
| 5,888,951 A | * | 3/1999 | Gagnebien et al. | 510/130 |

OTHER PUBLICATIONS

XP 002121409 Abstract of Database WPI Section Ch, Week 198938 Derwent Publications Ltd., London Feb. 1988.

XP 002121410 Abstract of Database WPI Section Ch, Week 199220 Derwent Publications Ltd., London Aug. 1990.

XP 002121407 Abstract of Chemical Abstracts, vol. 123, No. 6, Aug. 7, 1995.

Derwent Abstract of EP 0 384 983 A2 Sep. 1990.

Derwent Abstract of DE 43 27 700 A1 Feb. 1995.

Derwent Abstract of DE 43 06 899 A1 Sep 1994.

Derwent Abstract of EP 0 678 294 A2 Oct. 1995.

Derwent Abstract of EP 0 603 078 A1 Jun. 1994.

Abstract of JP 96,999 Mar. 1992.

Abstract of JP 112,819 Apr. 1992.

* cited by examiner

COSMETIC AND DERMATOLOGICAL DETERSIVE PREPARATIONS CONTAINING ACRYLATE COPOLYMERS, ALKYL GLUCOSIDES AND ALCOHOLS The present invention relates to cosmetic cleansers. Such products are known per se. They are essentially surface-active substances or mixtures of substances which are offered to the consumer in a variety of preparations.

Examples of preparations of this type are foam baths, shower gels, solid and liquid soaps or so-called "syndets" (synthetic detergents), shampoos, hand-washing pastes, personal hygiene products, special cleansers for small children, and the like.

Surface-active substances—the best known being the alkali metal salts of higher fatty acids, i.e. the classical "soaps"—are amphiphilic substances capable of emulsifying organic nonpolar substances in water.

These substances not only wash dirt from skin and hair, but also irritate the skin and mucosae to a greater or lesser extent depending on the choice of surfactant or surfactant mixture.

The surfactant used most widely for cosmetic compositions is sodium lauryl ether sulphate. Although it has good detergency and is well tolerated by the skin and mucosae, people with senstive skin should avoid frequent contact with it.

Although a large number of very mild surfactants is available, the surfactants of the prior art are either mild but have poor cleansing properties, or they have good cleansing properties but irritate the skin or mucosae.

The object was therefore to remedy these problems.

The present invention relates, in a particular embodiment, to cleansing preparations for use as shower preparations.

Such preparations are also known per se. They are essentially surface-active substances or mixtures of substances which are offered to the consumer in a variety of preparations. Preparations of this type are generally notable for having a certain water content, although they can also be in the form of, for example, a concentrate.

In general, preparations intended for the shower only differ slightly, or not at all, from bath preparations, except for the fact that in the case of shower preparations, preference is given to products having a higher viscosity which do not run from the hand following removal from the container. This is of lesser practical importance in the case of bath preparations.

Even a simple bath of water without added surfactants will initially cause the horny layer of the skin to swell, the degree of swelling being dependent on, for example, the bathing time and temperature. Not only are water-soluble substances, e.g. water-soluble constituents of dirt, washed off, but endogenous substances of the skin which are responsible for the water-binding ability of the horny layer are also washed away. In addition, fats in the skin are also dissolved and washed away to a certain extent by endogenous surface-active substances of the skin. After the initial swelling, this causes the skin to dry out significantly, which can be further intensified by detersive additives.

In healthy skin, these processes are generally of no consequence since the protective mechanisms of the skin can readily compensate for such slight disturbances to the upper layers of the skin. However, even in the case of non-pathological deviations from the norm, e.g. as a result of damage or irritation caused by the environment, light damage, ageing skin etc., the protective mechanism of the surface of the skin is disturbed. In some circumstances, it is then no longer able to fulfil its role by itself and must be regenerated using external measures.

The object of the present invention was thus to remedy these shortcomings of the prior art. It was also an object of the invention to provide bath and shower preparations which, on the one hand, are very gentle, but whose cleansing action, on the other hand, is not inferior.

The present invention further relates to detersive hair cosmetic preparations, commonly known as shampoos. In particular, the present invention relates to hair cosmetic active substance combinations and preparations for caring for the hair and the scalp.

BRIEF DESCRIPTION OF THE DRAWING

The invention will now be described in greater detail with reference to the drawing, wherein.

Figure 1:
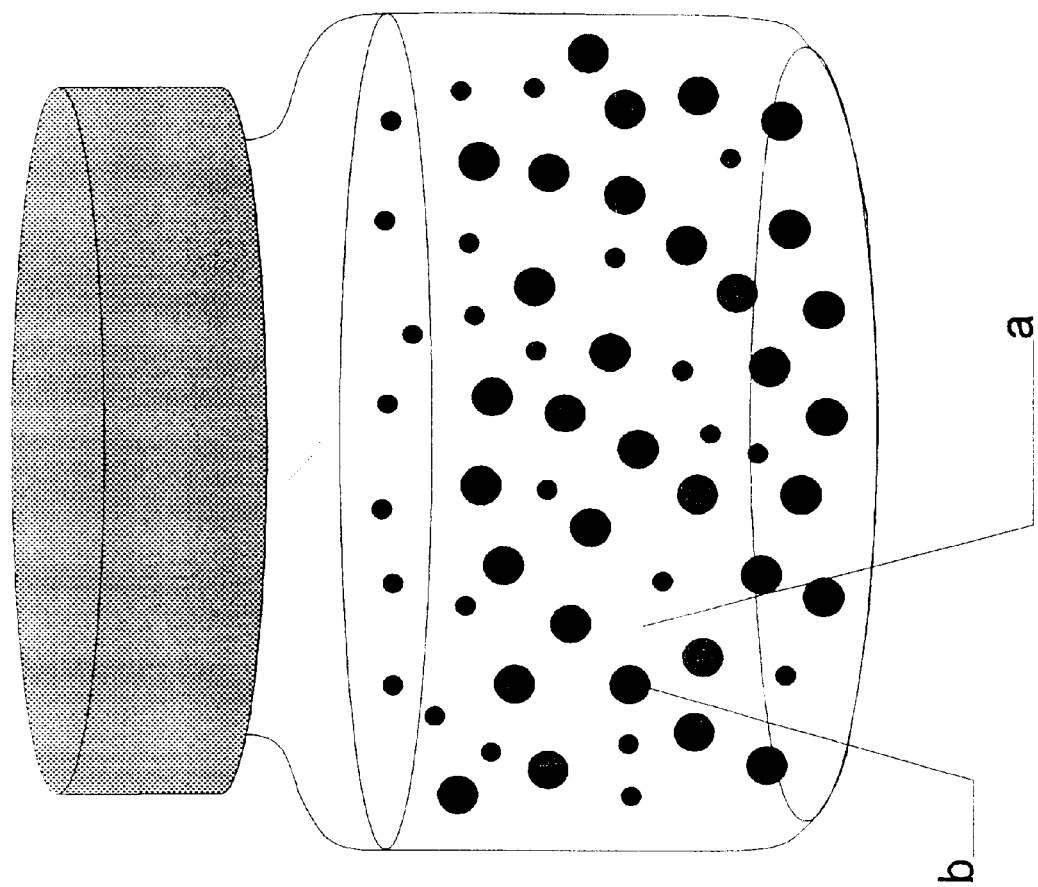
FIG. 1 is a depiction of an essentially clear gel.

The washing of hair with aggressive surfactants can stress the hair, at the very least diminishing its overall appearance or the appearance of the hair style. For example, certain water-soluble constituents of the hair (e.g. urea, uric acid, xanthine, keratin, glycogen, citric acid and lactic acid) can be leached out of the hair through washing.

There is, however, a lack of prior art shampoo formulations which care for the damaged hair in a satisfactory manner. It was thus the object also to remedy these disadvantages of the prior art.

Customary cosmetic and dermatological preparation forms which are also becoming ever more widespread, especially recently, are gels.

Cosmetic gels enjoy immense popularity amongst consumers. Since most of them are transparent, often coloured or may just as often be colourless and clear, they offer the cosmetics developer additional design opportunities, some of which are functional in character, whilst some are merely used to improve the external appearance Thus, it is, for example, possible to impart interesting optical effects to the product, which is then usually offered to the observer in transparent packaging, using incorporated pigments, gas bubbles and the like, or alternatively, larger objects.

It is desirable that these objects remain stationary in the gel formulation and do not sink to the bottom or migrate undesirably in any other way in the formulations, especially if it is desired that the incorporated object(s)—be they discernable as such with the naked eye, or be they present in microscopic dimensions, but arranged interestingly—for example in the form of artificially produced coloured swirls—should produce visible shapes. This is shown in FIG. 1, in which the reference a denotes an essentially clear gel in which discrete particles b, which are discernible with the naked eye, have been incorporated.

Liquids can differ in their rheological properties as a result of their flow and deformation behaviour. As a result of external forces, ideally elastic bodies undergo elastic deformation which spontaneously and completely reverses when the external force is removed. The shape of ideally viscous bodies is changed irreversibly as a result of external forces. The increasing deformation is termed flow. Most liquids are neither ideally viscous nor ideally elastic, but show both viscous and elastic properties and are thus termed viscoelastic substances.

In the large majority of viscoelastic solutions, dispersed particles or gas bubbles will always sink or rise respectively. They have an ultimate structural relaxation time. This means that the networks in these systems react to a deformation with a corresponding shear stress. However, this will relax to zero in a finite time so that the whole solution reverts to a stable steady state without strain. This also means that these solutions have a defined zero-shear viscosity and thus reach a constant viscosity at low shear rates.

In contrast to these systems, however, there are also those in which dispersed particles or gas bubbles do not sediment. It is noticeable that these systems only flow above a characteristic value. This value is called the flow limit. Closer inspection of the rheological properties of these systems indicates that the storage modulus is independent of the oscillation frequency over the whole frequency range and is always significantly greater than the loss modulus.

By contrast, the complex viscosity does not reach a constant value even at the lowest frequencies, but continues to increase.

Carbopol gels are crosslinked acrylic acid polymers having a large number of carboxyl groups. In dissolved form, these structures bind water. Neutralization of the carboxyl groups leads, as a result of their electrostatic repulsion, to expansion and thus swelling of the polymer chains. In this state the Carbopol gels achieve their typical rheological properties, such as, for example, the establishment of a flow limit.

The effect of establishing a flow limit is thus based on the electrostatic repulsion of the carboxyl groups. Additional electrolytes shield these charges. As a result, the networks collapse, the flow limit breaks down and particles or gas bubbles can no longer be held in suspension.

Surfactants act as electrolytes. It has thus to date not been possible to formulate high-foam cleansing products having a correspondingly high content of surfactant which contain, as base, clear Carbopol gels having a flow limit.

Although the prior art embraces corresponding systems containing xanthan gum (e.g. EP-A 738 509), they have poorer cosmetic properties in terms of the feel on the skin during and following application. Furthermore, it is only possible to obtain lower viscosities for the same use concentration. The formulation of a gel which has suitable flow properties does not usually present the expert with any major problems, except where high surfactant concentrations are desired—usually a basic requirement for cleansing products. The disadvantage of such high surfactant concentrations is that in most cases only hazy, cloudy or even opaque products are obtained.

A further object was thus to remedy this disadvantage of the prior art.

Surprisingly, it has been shown, and this is where the solution to these problems lies, that the prior art disadvantages are overcome by cosmetic and dermatological detersive preparations comprising (a) an effective amount of one or more surface-active substances selected from the group consisting of alkyl glucosides, which have the structural formula

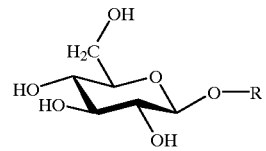

where R is a branched or unbranched alkyl radical having from 1 to 24 carbon atoms, (b) an effective amount of one or more gel-forming acrylate-alkyl acrylate copolymers and (c) branched and/or unbranched aliphatic alcohols having 2–6 carbon atoms and one or more OH functions.

It could therefore not have been foreseen by the expert that the preparations according to the invention would form clear gels with excellent rheological properties which would, moreover, also be highly suitable as detersive substances.

R in the structural formula of the alkyl glucoside is advantageously selected from the group consisting of unbranched alkyl radicals, preferably the hexyl, heptyl, octyl, nonyl, decyl, undecyl, dodecyl and tetradecyl radicals.

The total amount of one or more surface-active alkyl glucosides used according to the invention in the finished cosmetic or dermatological preparations is advantageously selected from the range 0.1–25.0% by weight, preferably 0.5–15.0% by weight, based on the total weight of the preparations.

The acrylate-alkyl acrylate copolymer(s) advantageously to be used according to the invention are advantageously selected from the group of so-called carbomers or Carbopols (Carbopol®: registered trademark of BFGoodrich Company). In particular, the acrylate-alkyl acrylate copolymer(s) advantageously to be used according to the invention are characterized by the following structure:

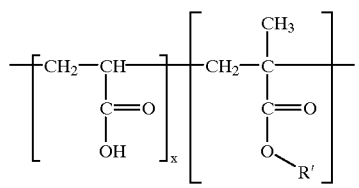

where R' is a long-chain alkyl radical and x and y are numbers which symbolize the respective stoichiometric amount of each of the comonomers.

Examples of acrylate-alkyl acrylate copolymers which can advantageously be used are products such as Carbopol® 1382 from the BFGoodrich Company.

The total amount of one or more surface-active acrylate-alkyl acrylate copolymers used according to the invention in the finished cosmetic or dermatological preparations is advantageously selected from the range 0.1–10.0% by weight, preferably 0.5–2.5% by weight, based on the total weight of the preparations.

In accordance with the invention, the alcohols are preferably selected from the group consisting of ethanol, ethylene glycol, propylene glycol, glycerol, isopropyl alcohol, 1,3-butylene glycol and 2,3-butylene glycol.

The preparations according to the invention are particularly preferably characterized by the fact that the total amount of one or more alcohols used according to the invention in the finished cosmetic or dermatological preparations is selected from the range 0.1–25.0% by weight, preferably 0.5–15.0% by weight, based on the total weight of the preparations.

The detersive preparations according to the invention are usually characterized by a water content of 95–5% by weight, based on the total weight of the preparations, and are gels.

The cosmetic and dermatological preparations according to the invention may contain cosmetic auxiliaries, such as those customarily used in such preparations, e.g. preservatives, bactericides, perfumes, antifoams, dyes, pigments which have a colouring effect, thickeners, moisturizers and/or humectants, fats, oils, waxes or other customary constituents of a cosmetic or dermatological formulation, such as alcohols, polyols, polymers, foam-stabilizers, electrolytes, organic solvents or silicone derivatives.

An additional content of antioxidants is generally preferred. According to the invention, favourable antioxidants are all those which are suitable or customary for cosmetic and/or dermatological applications.

The antioxidants are advantageously selected from the group consisting of amino acids (e.g. glycol, histidine, tyrosine, tryptophan) and derivatives thereof, imidazoles (e.g. urocanic acid, and derivatives thereof, peptides such as D,L-carnosine, D-carnosine, L-carnosine and derivatives thereof (e.g. anserine), carotenoids, carotenes (e.g.

α-carotene, β-carotene, γ-lycopine) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoeyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (e.g. buthionine sulphoximines, homocysteine sulphoximine, buthionine sulphones, penta-, hexa-, heptathionine sulphoximine) in very low tolerated doses (e.g. pmol to μmol/kg), also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, furfurylidene sorbitol and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferylbenzoate of benzoin, rutinic acid and derivatives thereof, α-glycosylrutin, ferulic acid, furfurylideneglucitol, carnosine, butylhydroxytoluene, butylhydroxyanisole, nordihydroguaiac acid, nordihydroguaiaretic acid, trihydroxybutyrophenone, uric acid and derivatives thereof, mannose and derivatives thereof, zinc and derivatives thereof (e.g. ZnO, ZnSO$_4$), selenium and derivatives thereof (e.g. selenium methionine), stilbenes and derivatives thereof (e.g. stilbene oxide, trans-stilbene oxide) and the derivatives of these specified active substances which are suitable according to the invention (salts, esters, ethers, sugars, nucleotides, nucleosides, peptides and lipids).

The amount of the above antioxidants (one or more compounds) in the preparations is preferably from 0.001 to 30% by weight, particularly preferably 0.05–20% by weight, in particular 1–10% by weight, based on the total weight of the preparation.

If vitamin E and/or derivatives thereof are used as the antioxidant(s), it is advantageous to choose their respective concentrations from the range 0.001–10% by weight, based on the total weight of the formulation.

If vitamin A or vitamin A derivatives, or carotenes or derivatives thereof are used as the antioxidant(s), it is advantageous to choose their respective concentrations from the range 0.001–10% by weight, based on the total weight of the formulation.

The cosmetic and/or dermatological preparations according to the invention are prepared in a manner familiar to the expert, which in most cases involves suspending and, if desired, homogenizing the surface-active glucose derivatives used according to the invention, with uniform stirring and, optionally, with warming, optionally combining them with further lipid components and optionally with one or more further emulsifiers, after which the oil phase is mixed with the aqueous phase, into which a thickener has optionally been incorporated and which preferably has roughly the same temperature as the oil phase, optionally homogenized and left to cool to room temperature. After the mixture has cooled to room temperature, it is possible to carry out further homogenization, particularly if volatile constituents are also to be incorporated.

The preparations according to the invention are particularly advantageously characterized by the fact that gaseous, solid and/or liquid objects are embedded in the gels. The expert is familiar with how such objects can be incorporated into the preparation.

The following examples are intended to illustrate the present invention, without limiting it. Unless stated otherwise, all quantities, proportions and percentages are based on the weight and the total amount or on the total weight of the preparations.

EXAMPLE 1

| | % by weight |
|---|---|
| Decyl glucoside (50%) | 20.00 |
| Carbopol ® 1382 | 1.50 |
| Sodium hydroxide | 0.75 |
| Butylene glycol | 10.00 |
| Propylene glycol | 17.50 |
| ZnSO$_4$ | 0.01 |
| Liquorice root extract | 0.10 |
| Calcium pantothenate | 0.10 |
| Na$_3$HEDTA | 0.50 |
| Camomile extract | 0.10 |
| Perfume, preservative | q.s. |
| Water | ad 100.00 |

EXAMPLE 2

| | % by weight |
|---|---|
| Decyl glucoside (50%) | 20.00 |
| Carbopol ® 1382 | 1.50 |
| Sodium hydroxide | 0.63 |
| Butylene glycol | 10.00 |
| Propylene glycol | 17.50 |
| ZnSO$_4$ | 0.01 |
| Liquorice root extract | 0.10 |
| Calcium pantothenate | 0.10 |
| Na$_3$HEDTA | 0.50 |
| Camomile extract | 0.10 |
| Perfume, preservative | q.s. |
| Water | ad 100.00 |

EXAMPLE 3

| | % by weight |
|---|---|
| Decyl glucoside (50%) | 20.00 |
| Carbopol ® 1382 | 1.25 |
| Sodium hydroxide | 0.65 |
| Butylene glycol | 10.00 |
| Ethanol | 11.00 |
| Na$_3$HEDTA | 1.00 |
| Perfume, preservative | q.s. |
| Water | ad 100.00 |

EXAMPLE 4

| | % by weight |
|---|---|
| Decyl glucoside (50%) | 10.00 |
| Carbopol ® 1382 | 0.75 |
| Sodium hydroxide | 0.35 |
| Butylene glycol | 10.00 |
| Propylene glycol | 11.00 |

-continued

| | % by weight |
|---|---|
| Na₃HEDTA | 0.50 |
| Perfume, preservative | q.s. |
| Water | ad 100.00 |

EXAMPLE 5

| | % by weight |
|---|---|
| Decyl glucoside (50%) | 20.00 |
| Carbopol ® 1382 | 1.00 |
| Sodium hydroxide | 0.50 |
| Butylene glycol | 10.00 |
| Propylene glycol | 17.50 |
| Na₃HEDTA | 0.50 |
| Perfume, preservative | q.s. |
| Water | ad 100.00 |

EXAMPLE 6

| | % by weight |
|---|---|
| Decyl glucoside (50%) | 30.00 |
| Carbopol ® 1382 | 1.25 |
| Sodium hydroxide | 0.50 |
| Butylene glycol | 5.00 |
| Propylene glycol | 17.50 |
| Na₃HEDTA | 0.50 |
| Perfume, preservative | q.s. |
| Water | ad 100.00 |

What is claimed is:

1. A method of cleansing an exterior portion of a human or animal body, said method comprising applying a shower or bath preparation to said exterior portion of said human or animal body, said shower or bath preparation comprising the following ingredients:
   a) 0.1 to 25% by weight based on the total weight of the preparation of one or more surface-active substances selected from the group consisting of alkyl glucosides of the formula:

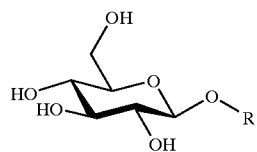

wherein R is a branched or unbranched alkyl radical having 1 to 24 carbon atoms;
   b) 0.1 to 10% by weight based on the total weight of the preparation of one or more gel-forming acrylate-alkyl acrylate copolymers, said gel-forming acrylate-alkyl acrylate copolymers comprising both acrylate structural units and alkyl acrylate structural units; and
   c) 0.1 to 25% by weight based on the total weight of the preparation of one or more branched or unbranched aliphatic alcohols having 2 to 6 carbon atoms and one or more hydroxyl groups;

said shower or bath preparation being in the form of a clear gel.

2. The method according to claim 1, wherein R is selected from the group consisting of unbranched alkyl radicals.

3. The method according to claim 2, wherein R is an unbranched alkyl radical selected from the group consisting of hexyl, heptyl, octyl, nonyl, decyl, undecyl, dodecyl and tetradecyl.

4. The method according to claim 1, wherein ingredient a) is present in said preparation in an amount ranging from 0.5 to 15% by weight based on the total weight of the preparation.

5. The method according to claim 1, wherein the one or more aliphatic alcohols are selected from the group consisting of ethylene glycol, propylene glycol, glycerol, isopropyl alcohol, 1,3-butylene glycol and 2,3-butylene glycol.

6. The method according to claim 1, wherein ingredient b) is present in said preparation in an amount ranging from 0.5 to 2.5% by weight based on the total weight of the preparation.

7. The method according to claim 1, wherein ingredient c) is present in said preparation in an amount ranging from 0.5 to 15% by weight based on the total weight of the preparation.

8. The method according to claim 1, wherein said one or more gel-forming acrylate-alkyl acrylate copolymers comprise both acrylate structural units of the formula:

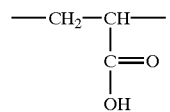

and alkyl acrylate structural units of the formula:

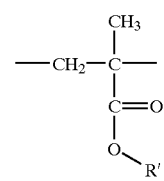

wherein R' is a long-chain alkyl radical.

9. The method according to claim 1, wherein the shower or bath preparation is in the form of a shampoo.

10. The method according to any one of claims 1–9, wherein the shower or bath preparation is applied to hair.

11. The method according to any one of claims 1–8, wherein the shower or bath preparation is applied to exterior skin.

* * * * *

UNITED STATES PATENT AND TRADEMARK OFFICE
CERTIFICATE OF CORRECTION

PATENT NO. : 6,706,673 B2
DATED : March 16, 2004
INVENTOR(S) : Lerg et al.

It is certified that error appears in the above-identified patent and that said Letters Patent is hereby corrected as shown below:

Column 6,
Line 31, "Carbopol ® 1382   1.50" should read -- Carbopol ® 1382   1.25 --

Signed and Sealed this

Fourteenth Day of December, 2004

JON W. DUDAS
*Director of the United States Patent and Trademark Office*